(12) United States Patent
Okumura et al.

(10) Patent No.: US 11,154,202 B2
(45) Date of Patent: Oct. 26, 2021

(54) MANAGEMENT METHOD OF PATCH, MANAGEMENT MODULE OF PATCH, AND PATCH DEVICE

(71) Applicant: NITTO DENKO CORPORATION, Osaka (JP)

(72) Inventors: Keisuke Okumura, Osaka (JP); Ryoma Yoshioka, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 258 days.

(21) Appl. No.: 16/087,935

(22) PCT Filed: Feb. 3, 2017

(86) PCT No.: PCT/JP2017/004007
§ 371 (c)(1),
(2) Date: Sep. 24, 2018

(87) PCT Pub. No.: WO2017/169108
PCT Pub. Date: Oct. 5, 2017

(65) Prior Publication Data
US 2019/0344061 A1   Nov. 14, 2019

(30) Foreign Application Priority Data

Mar. 30, 2016 (JP) .............................. JP2016-067472

(51) Int. Cl.
*A61B 5/01* (2006.01)
*A61M 35/00* (2006.01)

(52) U.S. Cl.
CPC ............... *A61B 5/01* (2013.01); *A61M 35/00* (2013.01); *A61M 35/10* (2019.05);
(Continued)

(58) Field of Classification Search
CPC ......... A61B 5/01; A61M 35/10; A61M 35/00; A61M 2205/13; A61M 2205/3569;
(Continued)

(56) References Cited

U.S. PATENT DOCUMENTS

2007/0100666 A1* 5/2007 Stivoric ............... A61B 5/6833
705/3
2008/0021519 A1* 1/2008 De Geest ................. G08B 6/00
607/58
(Continued)

FOREIGN PATENT DOCUMENTS

| CN | 204520636 U | 8/2015 |
| JP | S58-177847 U | 11/1983 |

(Continued)

OTHER PUBLICATIONS

International Preliminary Report on Patentability issued by WIPO dated Oct. 2, 2018, in connection with International Patent Application No. PCT/JP2017/004007.

(Continued)

*Primary Examiner* — Andrew J Mensh
(74) *Attorney, Agent, or Firm* — Jean C. Edwards, Esq.; Edwards Neils LLC

(57) ABSTRACT

A management method of a patch for managing a sticking state of a patch with respect to an individual having a body temperature includes a step (1) of sticking the patch to the individual, a step (2) of detecting a temperature change caused by sticking the patch to the individual, and a step (3) of judging whether or not the patch is stuck to the individual based on a presence or absence of the temperature change.

5 Claims, 5 Drawing Sheets

(52) U.S. Cl.
CPC ............... *A61M 2205/13* (2013.01); *A61M 2205/3569* (2013.01); *A61M 2205/50* (2013.01); *A61M 2205/587* (2013.01); *A61M 2205/8293* (2013.01); *A61M 2230/50* (2013.01)

(58) Field of Classification Search
CPC ........ A61M 2205/50; A61M 2205/587; A61M 2205/8293; A61M 2230/50
USPC ........................................................ 604/307
See application file for complete search history.

(56) References Cited

U.S. PATENT DOCUMENTS

| | | | | |
|---|---|---|---|---|
| 2009/0076349 | A1* | 3/2009 | Libbus | A61B 5/0006 600/301 |
| 2012/0245439 | A1* | 9/2012 | Andre | A61B 5/412 600/310 |
| 2013/0123719 | A1* | 5/2013 | Mao | G06F 19/3456 604/304 |
| 2016/0242654 | A1* | 8/2016 | Quinlan | G16H 20/40 |

FOREIGN PATENT DOCUMENTS

| | | |
|---|---|---|
| JP | H04-504000 A | 7/1992 |
| JP | H08-219898 A | 8/1996 |
| JP | 2002-168930 A | 6/2002 |
| JP | 2004-008471 A | 1/2004 |
| JP | 2012-180348 A | 9/2012 |
| JP | 5186208 B2 | 4/2013 |
| JP | 2015-056597 A | 3/2015 |
| WO | 90/10854 A1 | 9/1990 |
| WO | WO-9010854 A1 * | 9/1990 ............ G01K 13/002 |
| WO | 2013/142339 A1 | 9/2013 |
| WO | 2016/041873 A1 | 3/2016 |

OTHER PUBLICATIONS

Extended European Search Report issued by the European Patent Office dated Oct. 25, 2019, in connection with European Patent Application No. 17773657.6.

Office Action, issued by the Japanese Patent Office dated Feb. 25, 2020, in connection with Japanese Patent Application No. 2016-067472.

International Search Report Issued in PCT/JP2017/004007 dated Apr. 25, 2017.

Written Opinion Issued in PCT/JP2017/004007 dated Apr. 25, 2017.

Office Action, issued by the State Intellectual Property Office dated Oct. 28, 2020, in connection with Chinese Patent Application No. 201780019831.5.

Office Action, issued by the Japanese Patent Office dated Sep. 29, 2020, in connection with Japanese Patent Application No. 2016-067472.

\* cited by examiner

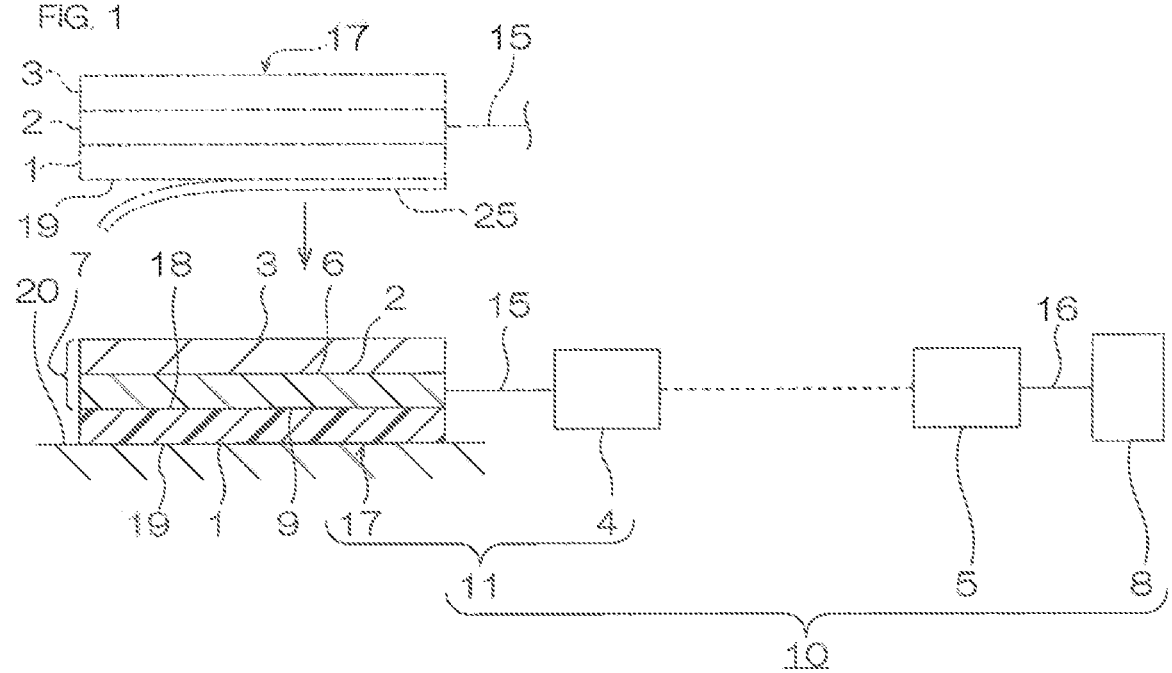

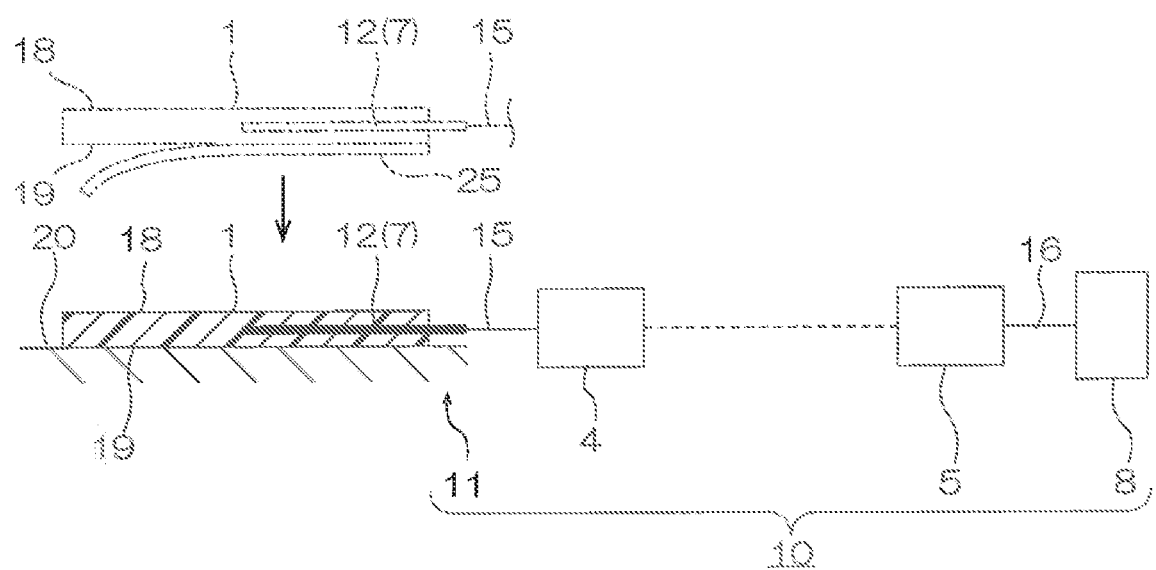

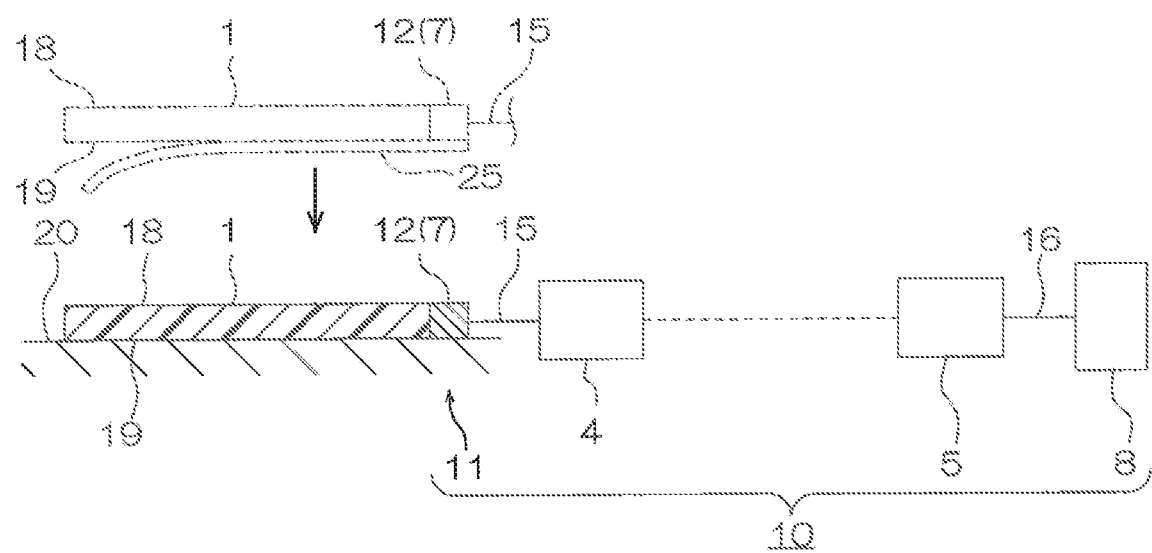

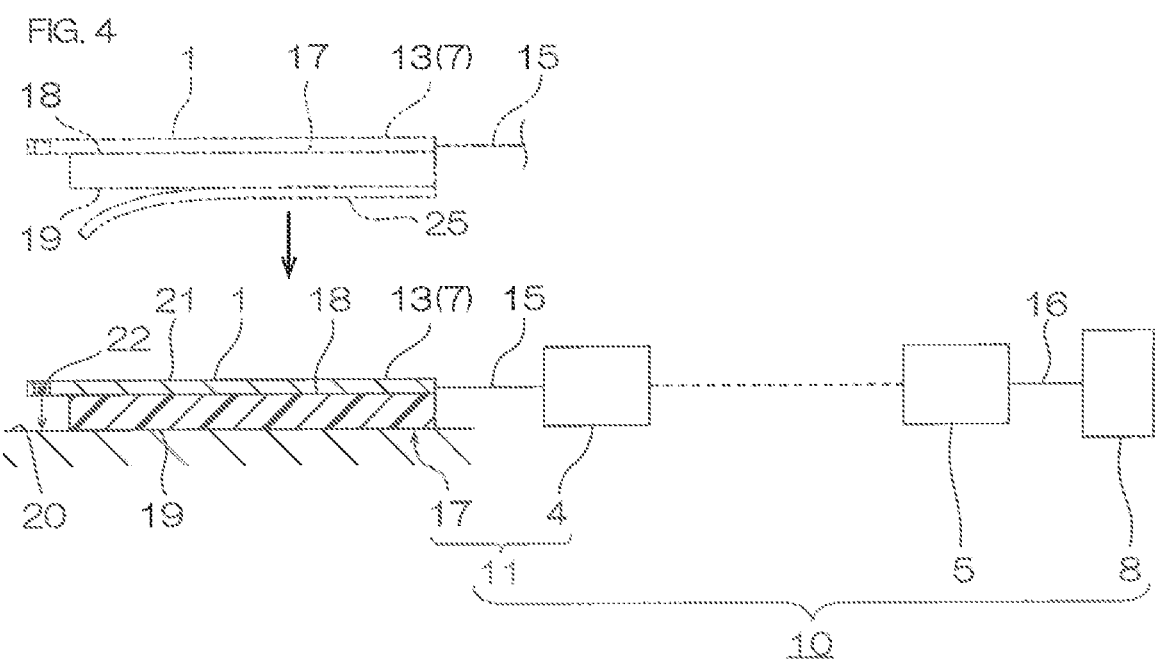

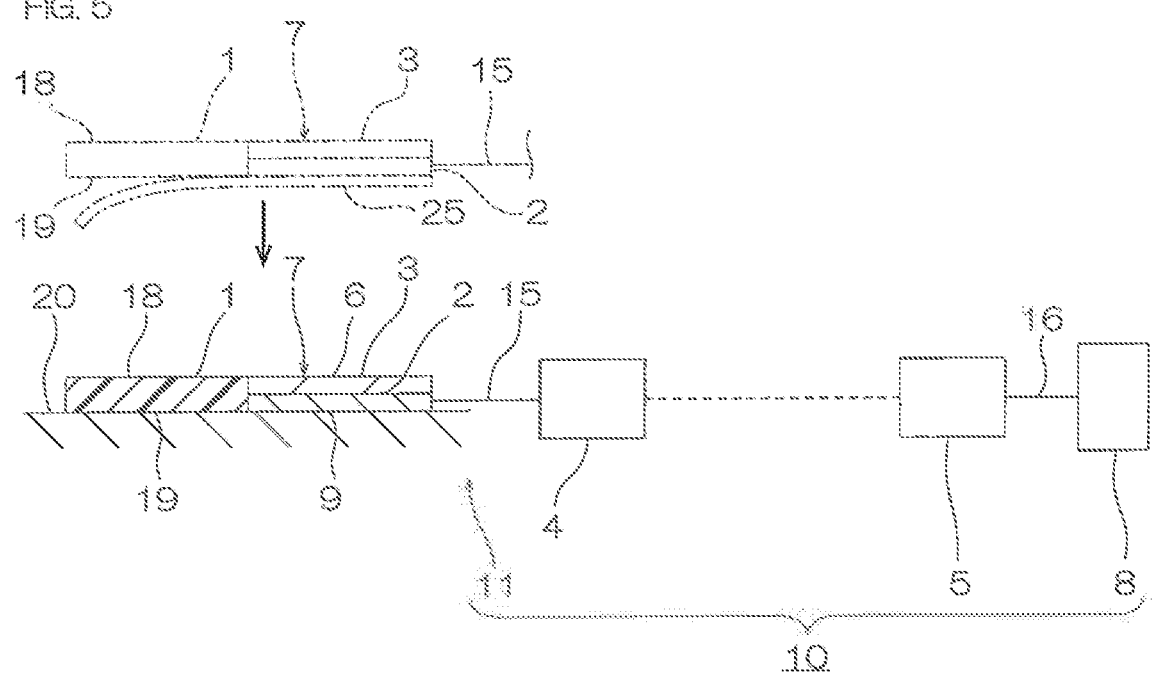

MANAGEMENT METHOD OF PATCH, MANAGEMENT MODULE OF PATCH, AND PATCH DEVICE

CROSS-REFERENCE TO RELATED APPLICATIONS

The present application is a 35 U.S.C. 371 National Stage Entry of PCT/JP2017/004007, filed on Feb. 3, 2017, which claims priority from Japanese Patent Application No. 2016-067472, filed on Mar. 30, 2016, the contents of all of which are herein incorporated by reference in their entirety.

TECHNICAL FIELD

The present invention relates to a management method of a patch, a management module of a patch, and a patch device, to be specific, to a management method of a patch, a patch device used therein, and a management module of a patch used in the management method of a patch.

BACKGROUND ART

A patch has been known as a pharmaceutical preparation used by being stuck to a patient. The patch is prescribed based on a doctor's prescription, and it is necessary for the patient to stick the patch by keeping the time and the number of times described in the prescription.

Considering the description above, for example, a method of informing a person of drug administration has been proposed (ref: for example, Patent Document 1).

The method of Patent Document 1 informs a person of the elapse of a predetermined time by using a checking device (biosensor) made by a support element including a series of body contacts, a pulse generator transmitting a series of pulses to the series of body contacts, and a power source into a patch in a state of sticking the device onto the skin of the person by allowing the device to perform a predetermined movement.

In the method of Patent Document 1, a warning is provided to a patient in which a stimulus such as electrical pulse, vibration, temperature change, or the like is given to the patient during an appropriate and optional period (interval or specific time) to the drug administration with the pulse generator, and the patch should be exchanged based on this.

Furthermore, in the method described in Patent Document 1, the biosensor measures a dissolved oxygen in blood passing through the skin, a pH of the skin, the level of protein, the level of glucose, the arterial pulse pressure, the enzyme content, the resistance of the skin, the electrical conductivity of the skin, or the like, and checks an effect of the drug in the patient.

CITATION LIST

Patent Document

Patent Document 1: Japanese Unexamined Patent Application No. 2012-180348

SUMMARY OF THE INVENTION

Problem to be Solved by the Invention

However, in the method described in Patent Document 1, there is a disadvantage that when the patient receives the warning from the pulse generator, it is not checked whether or not the patch is changed, so that it is practically impossible to check whether or not the patient keeps the prescription.

Also, there is a disadvantage that the biosensor described in Patent Document 1 measures a biological and chemical indicator in the patient by the patch, so that its structure is complicated.

An object of the present invention is to provide a management method of a patch capable of judging whether or not a patch is stuck to an individual in a simple structure, a patch device used therein, and a management module of a patch used in the management method of a patch.

Means for Solving the Problem

The present invention [1] includes a management method of a patch including a step (1) of sticking a patch to an individual, a step (2) of detecting a temperature change caused by sticking the patch to the individual, and a step (3) of judging whether or not the patch is stuck to the individual based on a presence or absence of the temperature change.

In the management method of a patch, by the step (2), the temperature change caused by sticking the patch to the individual is detected, and by the step (3), whether or not the patch is stuck to the individual is judged based on the presence or absence of the temperature change, so that whether or not the patch is stuck to the individual can be surely judged.

By the step (3), whether or not the patch is stuck to the individual is judged based on the presence or absence of the temperature change, so that the sticking of the patch to the individual can be easily judged.

The present invention [2] includes a management module of a patch used in the management method of a patch described in [1] including a patch for being stuck to an individual having a body temperature, a sensor detecting a temperature change caused by sticking the patch to the individual, and a judgement unit judging whether or not the patch is stuck to the individual based on the detection of the sensor.

According to the management module of a patch, the temperature change caused by sticking the patch to the individual can be easily detected with the sensor.

By the judgement unit, whether or not the patch is stuck to the individual can be surely judged based on the detection of the sensor.

The present invention [3] includes the management module of a patch described in [2] further including a transmitting device connected to the sensor and a receiving device connected to the judgement unit.

According to the management module of a patch, a signal based on the temperature change caused by sticking the patch to the individual is transmitted from the transmitting device to the receiving device. The signal reaches the judgement unit from the transmitting device, so that the judgement unit can surely judge whether or not the patch is stuck to the individual based on a presence or absence of the temperature change.

The present invention [4] includes a patch device used in the management method of a patch described in [1] including a patch for being stuck to an individual having a body temperature and a sensor detecting a temperature change caused by sticking the patch to the individual.

The patch device includes the patch for being stuck to the individual having a body temperature and the sensor detecting the temperature change caused by sticking the patch to the individual, so that the temperature change caused by sticking the patch to the individual can be detected with the sensor in a simple structure.

Also, whether or not the patch is stuck to the individual can be surely judged based on a presence or absence of the temperature change.

The present invention [5] includes the patch device described in [4], wherein the sensor includes a temperature changing member generating a temperature change caused by sticking the patch to the individual, and an output device outputting a detected signal based on the temperature change of the temperature changing member.

According to the patch device, the temperature changing member generates a temperature change caused by sticking the patch to the individual. Then, by the output device, the detected signal is output based on the temperature change of the temperature changing member, so that whether or not the patch is stuck to the individual can be surely judged based on the detected The present invention [6] includes the patch device described in [5], wherein the temperature changing member changes its state based on the temperature change, and the output device outputs the detected signal based on the state change.

According to the patch device, the temperature changing member changes its state based on the temperature change, so that a simple structure of the temperature changing member can be achieved compared to the biosensor of Patent Document 1 measuring the dissolved oxygen in blood, the pH of the skin, the level of protein, the level of glucose, the arterial pulse pressure, the enzyme content, the resistance of the skin, the electrical conductivity of the skin, or the like. Thus, the structure of the patch device can be simplified.

The present invention [7] includes the patch device described in [5] or [6], wherein heat from the individual is conducted to the temperature changing member via the patch.

In the patch device, the heat from the individual is conducted to the temperature changing member via the patch, so that a compact structure of the temperature changing member and the patch can be achieved.

The present invention [8] includes the patch device described in [7], wherein the temperature changing member is laminated in the patch.

According to the patch device, the temperature changing member is laminated in the patch, so that the patch device can be simply constituted from the temperature changing member and the patch. Also, the miniaturization of the patch device can be achieved.

The present invention [9] includes the patch device described in any one of [5] to [8], wherein the temperature changing member is made of a thermochromic resin having a light transmittance changeable according to a temperature change.

According to the patch device, the temperature changing member can change its light transmittance according to the temperature change. Thus, the temperature changing member can easily change its state based on the temperature change, The present invention [10] includes the patch device described in any one of [5] to [9], wherein the output device is an electromotive force generating device that generates an electromotive force based on the temperature change of the temperature changing member.

According to the patch device, the output device is the electromotive force generating device that generates the electromotive force based on the temperature change of the temperature changing member, so that the electromotive force generating device can surely output a detected signal based on the temperature change of the temperature changing member.

The present invention [11] includes the patch device described in [10], wherein the electromotive force generating device is a solar cell.

According to the patch device, the electromotive force generating device is the solar cell, so that the electromotive force generating device receives light, and can surely output a detected signal based on the temperature change of the temperature changing member.

The present invention [12] includes the patch device described in any one of [5] to [11], wherein the output device is laminated in the patch.

According to the patch device, the output device is laminated in the patch, so that the patch device can be simply constituted from the output device and the patch. Also, the miniaturization of the patch device can be achieved.

The present invention [13] includes the patch device described in any one of [5] to [12] further including a transmitting device connected to the output device.

The patch device further includes the transmitting device connected to the output device, so that a signal based on the temperature change caused by sticking the patch to the individual can be transmitted.

Effect of the Invention

The management method of a patch of the present invention can surely and easily judge whether or not the patch is stuck to the individual.

According to the management module of a patch of the present invention, the temperature change caused by sticking the patch to the individual can be easily detected with the sensor. Also, by the judgement unit, whether or not the patch is stuck to the individual can be surely judged based on the detection of the sensor.

According to the patch device of the present invention, the temperature change caused by sticking the patch to the individual can be detected in a simple structure. Also, whether or not the patch is stuck to the individual can be surely judged based on the presence or absence of the temperature change.

BRIEF DESCRIPTION OF THE DRAWINGS

FIG. 1 shows a schematic view of a first embodiment of a management module of a patch of the present invention.

FIG. 2 shows a schematic view of a second embodiment of a management module of a patch of the present invention.

FIG. 3 shows a schematic view of a modified example of the second embodiment shown in FIG. 2.

FIG. 4 shows a schematic view of a third embodiment of a management module of a patch of the present invention.

FIG. 5 shows a schematic view of a fourth embodiment of a management module of a patch of the present invention.

DESCRIPTION OF EMBODIMENTS

1. First Embodiment

A first embodiment of a management module of a patch (an adhesive skin patch, an adhesive preparation), and a patch device of the present invention is described.

As shown in FIG. 1, a management module 10 of a patch includes a patch device 11, a receiver 5 as one example of a receiving device and a judgement device $ as one example of a 1-1. Patch Device The patch device 11 has a flexible film shape (sheet shape). The patch device 11 includes a patch layer 1 as one example of a patch, a sensor 7, and a transmitter 4 as one example of a transmitting device.

1-1-1. Patch Layer

The patch layer 1 is a layer that is stuck to a patient 20 as one example of an individual having a body temperature. The patch layer 1 has a flexible film shape (sheet shape). The patch layer 1 constitutes the lower layer of a sensor-including patch laminate 17 (described later). The patch layer 1 has a first main surface (sticking surface) 19 stuck to the patient 20, and a second main surface 18 facing the first main surface 19. The patch layer 1 contains an adhesive medicinal component and a pressure-sensitive adhesive component.

The adhesive medicinal component is a pharmaceutical preparation for percutaneous absorption. To be specific, examples thereof include nonsteroidal antiinflammatory agent, sedative hypnotic, antihypertensive agent, hypotensive diuretic, antibiotic, anesthetic, antibacterial agent, antifungal agent, vitamin compound, coronary vasodilator, antihistaminic, antitussive, sex hormone, antidepressant, cerebral function activator, antiemtic, antitumor agent, antiepileptic, anti-Alzheimer agent, antiparkinsonian agent, antithrombotic agent, and biometric medicine. These adhesive medicinal components can be used alone or in combination of two or more.

The pressure-sensitive adhesive component is a component that imparts pressure-sensitive adhesive properties (stickiness) to the patch layer 1. Examples of the pressure-sensitive adhesive component include acrylic pressure-sensitive adhesive, rubber pressure-sensitive adhesive, silicone pressure-sensitive adhesive, vinyl ether pressure-sensitive adhesive, vinyl ester pressure-sensitive adhesive, and polyester pressure-sensitive adhesive.

The content ratio of the adhesive medicinal component and the pressure-sensitive adhesive component is set in a range in which the patch layer 1 achieves a percutaneous absorption function, and the pressure-sensitive adhesive properties of the patch layer 1 are not damaged. To be specific, the content ratio of the adhesive medicinal component with respect to the patch layer 1 is, for example, 0.1 mass % or more, preferably 0.5 mass % or more, and for example, 50 mass % or less, preferably 30 mass % or less. The content ratio of the pressure-sensitive adhesive component is a remaining portion of the above-described content ratio of the adhesive medicinal component.

The patch layer 1 can also contain a known additional component at an appropriate ratio.

The patch layer 1 can also contain a substrate layer that is no shown for retaining the mechanical strength of the patch layer 1.

The heat conductivity in a thickness direction of the patch layer 1 is, for example, 0.1 W/m·K or more, preferably 0.2 W/m·K, or more, more preferably 0.3 W/m·K or more, and for example, 1.0 W/m·K or less. When the heat conductivity in the thickness direction of the patch layer 1 is the above-described lower limit or more, the interruption of the heat conduction from the patient 20 to a thermochromic resin layer 3 can be suppressed, The thickness of a sticky agent in the patch layer 1 is, for example, 20 μm or more, preferably 30 μm or more, more preferably 50 μm or more. When the thickness of the patch layer 1 is the above-described lower limit or more, the sufficient percutaneous absorption function and the pressure-sensitive adhesive properties of the patch layer 1 can be ensured, The thickness of the patch layer 1 is, for example, 500 μm or less, preferably 300 μm or less, more preferably 100 μm or less. When the thickness of the patch layer 1 is the above-described upper limit or less, the interruption of the heat conduction from the patient 20 to the thermochromic resin layer 3 can be suppressed.

1-1-2. Sensor

The sensor 7 is provided on the upper surface of the patch layer 1. To be more specific, the sensor 7 is disposed on the entire upper surface of the patch layer 1. The sensor 7 is directly laminated in the patch layer 1 in the thickness direction. The sensor 7 has a flexible film shape (sheet shape). The sensor 7 includes a solar cell layer 2 as one example of an output device and the thermochromic resin layer 3 as one example of a temperature changing member. To be specific, in the sensor 7, the solar cell layer 2 and the thermochromic resin layer 3 are sequentially laminated on the patch layer 1. Preferably, the sensor 7 consists of only the solar cell layer 2 and the thermochromic resin layer 3.

1-1-3. Solar Cell Layer

The solar cell layer 2 is, for example, a solar cell made of a crystalline or amorphous silicon or the like. The solar cell layer 2 has a flexible film shape (sheet shape). The solar cell layer 2 has flexibility. The solar cell layer 2 is one example of an electromotive force generating device that generates an electromotive force by a change of light transmittance based on a temperature change of the thermochromic resin layer 3. The solar cell layer 2 can output an electromotive force as a detected signal.

The surface (one surface m the thickness direction) of the solar cell layer 2 is a light receiving surface (main surface) 6 capable of generating an electromotive force by receiving light. The solar cell layer 2 is a one surface-type solar cell that generates the electromotive force by receiving the light from the light receiving surface 6.

The solar cell layer 2 is laminated on the patch layer 1. The rear surface (the other surface in the thickness direction) of the solar cell layer 2 is a connecting surface (main surface) 9 bonded to the second main surface 18 of the patch layer 1. The connecting surface 9 of the solar cell layer 2 is in direct contact with the patch layer 1 to be bonded thereto.

The heat conductivity in the thickness direction of the solar cell layer 2 is, for example, 0.1 W/m·K or more, preferably 1 W/m·K or more, more preferably 3 W/m·K or more, and for example, 150 W/m·K or less. When the heat conductivity in the thickness direction of the solar cell layer 2 is the above-described lower limit or more, the interruption of the heat conduction from the patient 20 to the thermochromic resin layer 3 can be suppressed.

The thickness of the solar cell layer 2 is, for example, 50 μm or more, preferably 100 μm or more, more preferably 200 μm or more. When the thickness of the solar cell layer 2 is the above-described lower limit or more, the strength of the solar cell layer 2 can be ensured.

The thickness of the solar cell layer 2 is, far example, 2000 μm or less, preferably 1000 μm or less, more preferably 400 μm or less. When the thickness of the solar cell layer 2 is the above-described upper limit or less, the interruption of the heat conduction from the patient 20 to the thermochromic resin layer 3 can be suppressed.

The total thickness of the patch layer 1 and the solar cell layer 2 is, for example, 200 μm or more, preferably 300 μm or more. When the total thickness of the patch layer 1 and the solar cell layer 2 is the above-described lower limit or more, the mechanical strength of the sensor including patch laminate 17 can be sufficiently ensured.

The total thickness of the patch layer 1 and the solar cell layer 2 is, for example, 2500 μm or less, preferably 1300 μm or less, more preferably 500 μm or less. When the total thickness of the patch layer 1 and the solar cell layer 2 is the above-described upper limit or less, the interruption of the heat conduction from the patient 20 to the thermochromic resin layer 3 can be suppressed.

1-1-4. Thermochromic Resin Layer

The thermochromic resin layer 3 is disposed on the entire light receiving surface 6 of the solar cell layer 2. In this manner, the thermochromic resin layer 3 covers the solar cell layer 2. The thermochromic resin layer 3 is in direct contact with the light receiving surface 6 of the solar cell layer 2. The thermochromic resin layer 3 has a flexible film shape. The thermochromic resin layer 3 constitutes the upper layer of the sensor-including patch laminate 17 (described later). The thermochromic resin layer 3 is laminated in the patch layer 1 by sandwiching the solar cell layer 2 therebetween.

The thermochromic, resin layer 3 is formed from a resin composition having thermochromic properties (thermochromic resin) into a film shape.

The resin composition contains, for example, a resin and a thermochromic material. Examples of the resin include transparent resins such as silicone: resin, epoxy resin, and acrylic resin. An example of the thermochromic material includes the pigment. An example of the thermochromic pigment includes a heat sensitive material in which three components of an electron donative coloring organic compound, a compound having a phenolic hydroxyl group, and a compound having an alcoholic hydroxyl group are contained as an essential component (Japanese Examined Patent Publications No. S51-44706, No. S51-44707, No. H1-29398, or the like). The thermochromic material is a reversible thermochromic composition that changes its color before or after a predetermined temperature T (color changing point), is brought into a discoloring (colorless) state in a temperature region of a higher temperature-side color changing point or more, and is brought into a coloring (colored) state in a temperature region of below a lower temperature-side color changing point. To be specific, an example thereof includes a heat sensitive material (Example 4 of Japanese Examined Patent Publication No. S51-44706) that is made of crystal violet lactone (electron donative coloring organic compound), propyl ester gallate (compound having a phenolic hydroxyl group), and n-myristyl alcohol (compound having an alcoholic hydroxyl group), and its color changing point is 35° C. The above-described temperature T (color changing point) is appropriately selected by the formulation of each of the components described above. The mixing ratio of the thermochromic material with respect to 100 parts by mass of the resin is, for example, 1 part by mass or more, preferably 3 parts by mass or more, and for example, 25 parts by mass or less, preferably 15 parts by mass or less.

The thermochromic resin layer 3 has a thermochromic material, so that it has properties (thermochromic properties) of showing a thermochromic phenomenon in which a light transmittance reversibly changes in accordance with the above-described temperature change. Meanwhile, at the temperature T (° C.) (color changing point of the thermochromic material) or more, the thermochromic resin layer 3 has a high light transmittance, for example, depends on the illuminance of light applied to the thermochromic resin layer 3, and has a light transmittance that generates an electromotive force in the solar cell layer 2 when the light transmits the thermochromic resin layer 3.

To be specific, the ratio (T2/T1) of a light transmittance T2 of the thermochromic resin layer 3 at the temperature T (° C.) (color changing point of the thermochromic material) or more to a light transmittance T1 of the thermochromic resin layer 3 at below the temperature T (° C.) (color changing point of the thermochromic material) is, for example, above 1.00, preferably 1.05 or more, more preferably 1.20 or more, further more preferably 1.50 or more. The light transmittance is a transmittance of visible light (400 to 700 nm). The light transmittance is measured with CM-700d manufactured by Konica Minolta, Inc. The light transmittance at the temperature T is a light transmittance that allows the transmission of the minimum light necessary for generation of the electromotive force of the solar cell layer 2.

The above-described temperature T is determined in accordance with the type of the thermochromic material. To be specific, the temperature T is, for example, 30° C. or more, preferably 32° C. or more, more preferably 34° C. or more, and for example, 40° C., or less.

The thickness of the thermochromic resin layer 3 is, for example, 5 μm or more, preferably 25 μm or more, and for example, 1000 μm or less, preferably 250 μm or less.

The patch layer 1 and the sensor 7 constitute the sensor-including patch laminate 17. The sensor-including patch laminate 17 sequentially includes the patch layer 1, the solar cell layer 2, and the thermochromic resin layer 3 in the thickness direction. That is, the sensor-including patch laminate 17 includes the patch layer 1, the solar cell layer 2 that is disposed thereon, and the thermochromic resin layer 3 that is disposed thereon. The sensor-including patch laminate 17 can also include a peeling sheet 25 that is laminated on the first main surface 19 of the patch layer 1. The peeling sheet 25 is laminated on the first main surface 19 of the patch layer 1 until immediately before the patch layer 1 is stuck to the patient 20.

1-1-5. Transmitter

The transmitter 4 is electrically connected to the sensor 7. To be specific, the transmitter 4 is electrically connected to the solar cell layer 2. To be more specific, the transmitter 4 is connected to the solar cell layer 2 via a first wire 15. The transmitter 4 is constituted to detect the electromotive force generated in the solar cell layer 2 as a detected signal, and to wirelessly transmit a patch signal to the receiver 5 by using the electromotive force as an electric power. That is, the transmitter 4 is operated by the electric power directly supplied from the solar cell layer 2.

The transmitter 4 is positioned in the neighborhood of the sensor 7. The transmitter 4 includes, for example, a generating element that generates the patch signal from the detected signal based on the electromotive force generated in the solar cell layer 2, and a transmitting antenna (not shown) that is capable of wirelessly transmitting the patch signal generated in the generating dement.

1-2. Receiver

The receiver 5 is disposed in a remote position with respect to the patch device 11.

The receiver 5 includes, for example, a receiving antenna (not shown) capable of receiving a patch signal wirelessly transmitted from the transmitter 4 of the patch device 11, and an amplifier (not shown) that amplifies the patch signal received by the receiving antenna.

1-3. Judgement Unit

The judgement device 8 is electrically connected to the receiver 5. To be specific, the judgement device 8 is electrically connected to the receiver 5 via a second wire 16.

The judgement device 8 is, for example, disposed under the management of an administrator. Examples of the administrator include family of the patient 20 and medical workers. When the administrator is a medical worker, the judgement unit 8 is disposed at the inside of a management facility such as medical center.

The judgement device 8 includes, for example, CPU (not shown) that judges whether or not the patch layer 1 is stuck to the patient 20 based on the patch signal amplified in the receiver 5, and an information device (not shown) of informing the administrator of the result that is judged by the CPU. Examples of the information device include monitor and speaker.

1-4. Management Method of Patch

Next, a first embodiment of a management method of a patch of the present invention is described.

The management method of a patch is a method of managing a sticking state of the patch layer 1 with respect to the patient 20. The management method of a patch includes a step (1) of sticking the patch layer 1 to the patient 20, a step (2) of detecting a temperature change caused by sticking the patch layer 1 to the patient 20, and a step (3) of judging whether or not the patch 1 is stuck to the patient 20 based on a presence or absence of the temperature change. In the following, each of the steps is described.

1-4-1. Step (1)

In the step (1), the patch layer 1 is stuck to the patient 20.

First, the patch layer 1 is stuck to the patient 20 under the management of the above-described management module 10 of a patch.

To be specific, first, as shown by a phantom line of FIG. 1, the patch device 11 including the sensor-including patch laminate 17 that sequentially includes the peeling sheet 25, the patch layer 1, the solar cell layer 2, and the thermochromic resin layer 3, and the transmitter 4 that is connected to the solar cell layer 2 of the sensor-including patch laminate 17 is prepared. The patch layer 1 is pharmaceutically prepared based on a prescription of a doctor. The sensor 7 is laminated in the patch layer 1, so that the sensor-including patch laminate 17 is prepared.

Separately, the receiver 5 and the judgement device 8 are disposed in the neighborhood of the administrator.

Next, the peeling sheet 25 is peeled from the first main surface 19 of the patch layer 1, and the first main surface 19 of the patch layer 1 is exposed.

The thermochromic resin layer 3 is not yet in contact with the patient 20 until the first main surface 19 of the patch layer 1 is stuck to the skin of the patient 20, so that the temperature of the thermochromic resin layer 3 is low (below the temperature T (color changing point of the thermochromic material)), and the light transmittance of the thermochromic resin layer 3 is low. Thus, in the sensor 7, the thermochromic resin layer 3 shields light to the solar cell layer 2. Accordingly, the solar cell layer 2 does not generate an electromotive force (does not output a detected signal), and the transmitter 4 does not transmit a signal (patch signal) of sticking the patch layer 1 to the patient 20. Thus, the receiver 5 does not receive the signal (patch signal). Accordingly, in the judgement device 8, the CPU judges that the patch layer 1 is not yet stuck m the patient 20, and the information device does not inform the administrator of the sticking of the temperature sensor 1 to the patch layer 1.

Thereafter, the first main surface 19 of the patch layer 1 is stuck to the skin of the patient 20.

1-4-2. Step (2)

In the step (2), the temperature change caused by sticking the patch layer 1 to the patient 20 is detected with the sensor 7.

To be specific, when the patch layer 1 is stuck to the patient 20, heat from the patient 20 is conducted to the thermochromic resin layer 3 via the patch layer 1 and the solar cell layer 2.

Then, the temperature of the thermochromic resin layer 3 is increased (the temperature T (color changing point of the thermochromic material) or more), so that the light transmittance of the thermochromic resin layer 3 is increased. To be specific, the thermochromic resin layer 3 has a high light transmittance of generating an electromotive force in the solar cell layer 2. Thus, the light transmits the thermochromic resin layer 3.

At this time, the solar cell layer 2 receives the light, and generates the electromotive force. The solar cell layer 2 outputs the electromotive force as a detected signal.

The transmitter 4 generates a patch signal based on the-detected signal output from the solar cell layer 2, and the patch signal is wirelessly transmitted.

1-4-3. Step (3)

In the step (3), whether or not the patch layer 1 is stuck to the patient 20 is judged based on the presence or absence of the temperature change of the thermochromic resin layer 3.

To be specific, first the receiver 5 receives a patch signal wirelessly transmitted from the transmitter 4. Thereafter, in the judgement device 8, the CPU judges that the patch layer 1 is stuck to the patient 20 based on the patch signal received by the receiver 5, and the information device informs the administrator of the result.

In this manner, the sticking of the patch layer 1 to the patient 20 is managed by the administrator. To be specific, it is checked by the administrator whether or not the patch layer 1 is stack to the skin of the patient 20 in accordance with the number of times and the time described in the prescription.

1-5. Function and Effect of First Embodiment

In the management method of a patch, by the step (2), a temperature change (increase) caused by sticking the patch layer 1 to the patient 20 is detected, and by the step (3), whether or not the patch layer 1 is stuck to the patient 20 is judged based on a presence or absence of the temperature change, so that whether or not the patch layer 1 is stuck to the patient 20 can be surely judged.

By the step (3), whether or not the patch layer 1 is stuck to the patient 20 is judged based on the presence or absence of the temperature change, so that the sticking of the patch layer 1 to the patient 20 can be easily judged.

According to the management module 10 of a patch, the temperature change caused by sticking the patch layer 1 to the patient 20 can be easily detected with the sensor 7.

By the judgement device 8, whether or not the patch layer 1 is stuck to the patient 20 can be surely judged based on the detection of the sensor 7.

According to the management module 10 of a patch, a patch signal based on the temperature change caused by sticking the patch layer 1 to the patient 20 is transmitted from the transmitter 4 to the receiver 5. The patch signal reaches the judgement device 8 from the receiver 5, so that the judgement device 8 can surely judge whether or not the patch layer 1 is stuck to the patient 20.

The patch device 11 includes the patch layer 1 and the sensor 7, so that the temperature change caused by sticking the patch layer 1 to the patient 20 can be detected with the sensor 7 in a simple structure.

Also, whether or not the patch layer 1 is stuck to the patient 20 can be surely judged based on a presence or absence of the temperature change (increase).

According to the patch device 11, the thermochromic resin layer 3 generates a temperature change caused by sticking the patch layer 1 to the patient 20. Then, by the solar cell layer 2, an electromotive force is generated by a change (increase) of the light transmittance based on the temperature change (increase) of the thermochromic resin layer 3, so that whether or not the patch layer 1 is stuck to the patient 20 can be surely judged based on the electromotive force.

According to the patch device 11, the thermochromic resin layer 3 changes its state based on the temperature change (the light transmittance increases as the temperature is the color changing point or more), so that a simple structure of the thermochromic resin layer 3 can be achieved. Thus, the structure of the patch device 11 can be simplified.

In the patch device 11, the heat from the patient 20 is conducted to the thermochromic resin layer 3 via the patch layer 1, so that a compact structure of the thermochromic resin layer 3 and the patch layer 1 can be achieved.

According to the patch device 11, the thermochromic resin layer 3 is laminated in the patch layer 1, so that the patch device 11 can be simply constituted from the thermochromic resin layer 3 and the patch layer 1. Also, the miniaturization of the patch device 11 can be achieved. Furthermore, the size of the thermochromic resin layer 3 can be almost the same as that of the patch layer 1.

According to the patch device 11, the thermochromic resin layer 3 can change its light transmittance according to the temperature change. Thus, the thermochromic resin layer 3 can easily change its state based on the temperature change.

According to the patch device 11, the solar cell layer 2 is an electromotive force generating device that generates an electromotive force based on the temperature change of the thermochromic resin layer 3, so that the solar cell layer 2 can receive light transmitting the thermochromic resin layer 3, and surely output a detected signal as the electromotive force based on the temperature change of the thermochromic resin layer 3.

According to the patch device 11, the solar cell layer 2 is made of a solar cell, so that the solar cell layer 2 can surely output a detected signal based on the temperature change of the thermochromic resin layer 3.

According to the patch device 11, the solar cell layer 2 is laminated on the patch, so that the patch device 11 can be simply constituted from the solar cell layer 2 and the patch layer 1. Also, the miniaturization of the patch device 11 can be achieved. Furthermore, the size of the solar cell layer 2 can be almost the same as that of the patch layer 1.

The patch device 11 includes the transmitter 4 connected to the solar cell layer 2, so that the signal based on the temperature change caused by sticking the patch layer 1 to the patient 20 can be transmitted from the transmitter 4. Thus, a sticking state of the patch layer 1 with respect to the patient 20 can be surely managed.

1-6. Modified Example of First Embodiment

In the first embodiment, as shown in FIG. 1, the patch device 11 separately includes the receiver 5 and the judgement device 8.

Alternatively, though not shown, the patch device 11 can integrally include the receiver 5 and the judgement device 8. Although not shown, for example, the receiver 5 may be incorporated into the judgement device 8.

As one example of the individual having a body temperature, the patient 20 is used. Alternatively, for example, a person without having a disease may be also used. Also, as the individual having a body temperature, a homothermal animal (homeotherm) (excluding human beings) may be used.

In the first embodiment, the thermochromic resin layer 3 shields the light to the solar cell layer 2 at below the temperature T (color changing point of the thermochromic material). Alternatively, a part of the light may transmit the thermochromic resin layer 3, and the solar cell layer 2 may generate a first electromotive three. In such a case, the entire light or a part thereof transmits the thermochromic resin layer 3, the solar cell layer 2 generates a second electromotive force, and the transmitter 4 transmits a patch signal based on a difference between the two electromotive forces (second electromotive force first electromotive three) at the temperature T (color changing point of the thermochromic material) or more.

In the first embodiment, in the judgement unit 8, the information device informs that the patch layer 1 is stuck to the patient 20. Alternatively, for example, a recording device such as memory and recorder can be also used. In such a case, after recording, a sticking state of the patch layer 1 with respect to the patient 20 can be managed by checking the recording device by the administrator.

In the first embodiment, a case where the patch layer 1 is stuck to the patient 20 is judged. Furthermore, for example, a case where the patch layer 1 is removed from the patient 20 can be also judged. In such a case, in a state where the patch layer 1 is stuck to the patient 20, the temperature of the thermochromic resin layer 3 is high (the color changing point of the thermochromic material or more), so that the light transmittance of the thermochromic resin layer 3 retains high. Thus, the light transmits the thermochromic resin layer 3, and the solar cell layer 2 continues to generate the electromotive force, so that the transmitter 4 continuously transmits the patch signal, the receiver 5 continuously receives the patch signal, and the judgement unit 8 judges that the patch layer 1 is in a state of being stuck to the patient 20.

Thereafter, when the patch layer 1 is removed from the patient 20, the temperature of the thermochromic resin layer 3 is lowered (below the color changing point of the thermochromic material), so that the light transmittance of the thermochromic resin layer 3 is lowered. Thus, the generation of the electromotive force of the solar cell layer 2 stops, and the reception of the patch signal in the receiver 5 is discontinued. Then, the judgement unit 8 judges that the patch layer 1 is removed from the patient 20.

In short, the management module 10 of a patch can manage both of the sticking of the patch layer 1 to the patient 20 and the removal thereof.

2. Second Embodiment

In the second embodiment, the same reference numerals are provided for members and steps corresponding to each of those in the first embodiment, and their detailed description is omitted.

In the first embodiment, as shown in FIG. 1, the sensor 7 includes the solar cell layer 2 and the them-lock-oink resin layer 3.

Alternatively, in the second embodiment, as shown in FIG. 2, the sensor 7 includes a thermocouple thermometer 12. To be specific, the sensor 7 is the thermocouple thermometer 12.

2-1. Thermocouple Thermometer

The thermocouple thermometer 12 is a contact-type temperature sensor. The thermocouple thermometer 12 includes a thermocouple (temperature detecting end) (not shown) made of two types of metal wires (not shown) having one end thereof connected to each other, and a measuring element (not shown) measuring an electromotive force (electric voltage) generated in the thermocouple.

The thermocouple thermometer 12 functions as both a temperature changing member that generates a temperature change caused by sticking the patch layer 1 to the patient 20, and an output device that outputs a patch signal as one example of a detected signal based on the temperature change of the temperature changing member.

To be specific, the thermocouple (temperature detecting end) is the temperature changing member that changes the electromotive force (electric voltage) based on the temperature change. The measuring element is the output device that outputs the patch signal based on a change of the electromotive force of the thermocouple.

The thermocouple thermometer 12 is embedded in the patch layer 1. To be specific, the thermocouple thermometer 12 has a generally stick shape extending in a plane direction (right-left direction of FIG. 2), and is positioned between the first main surface 19 and the second main surface 18.

The other end portion of the thermocouple thermometer 12 is exposed from the patch layer 1. The first wire 15 is electrically connected to the other end portion of the thermocouple thermometer 12. The thermocouple thermometer 12 is connected to the transmitter 4 via the first wire 15.

2-2. Management Method of Patch (Step (2))

In the management method of a patch using the patch device 11 of the second embodiment, in the step (2), when the patch layer 1 is stuck to the patient 20, the heat of the patient 20 is conducted to the thermocouple thermometer 12 via the lower-side portion of the patch layer 1.

Then, an electromotive force (electric voltage) is generated in the thermocouple of the thermocouple thermometer 12.

At this time, in the thermocouple thermometer 12, the measuring element converts the above-described electromotive force (electric voltage) to the patch signal, and outputs it to the transmitter 4.

Thereafter, the transmitter 4 wirelessly transmits the patch signal.

In the second embodiment, the same function and effect as that of the first embodiment can be achieved.

2-3. Modified Example of Second Embodiment

In the second embodiment, as shown in FIG. 2, the thermocouple thermometer 12 is embedded in the patch layer 1.

Alternatively, as shown in FIG. 3, the thermocouple thermometer 12 may be disposed next to the patch layer 1.

The thermocouple thermometer 12 is in contact with one surface in the outer-side surface of the patch layer 1 (connecting surface that connects one end portion of the second main surface 18 to one end portion of the first main surface 19). The patch layer 1 and the thermocouple thermometer 12 are disposed in parallel in a first direction of the plane direction (right-left direction of FIG. 3). The thermocouple thermometer 12 extends in a second direction of the plane direction (direction perpendicular to the first direction of the plane direction and the thickness direction, depth direction of FIG. 3). In the step (1), the thermocouple thermometer 12 is also in contact with the patient 20.

3. Third Embodiment

In the third embodiment, the same reference numerals are provided for members and steps corresponding to each of those in the first and second embodiments, and their detailed description is omitted.

In the second embodiment, as shown in FIG. 2, the sensor 7 is the thermocouple thermometer 12.

Meanwhile, in the third embodiment, as shown in FIG. 3, the sensor 7 is a radiation thermometer 13.

3-1. Radiation Thermometer

The radiation thermometer 13 is a non-contact-type temperature sensor in which at least one of the infrared light and the visible light is applied to the patient 20 to measure the temperature of the skin of the patient 20. The radiation thermometer 13 has a main body 21 and an irradiation port 22 that is installed at the front end portion of the main body 21. In the main body 21, a portion excluding the front end portion is laminated on the second main surface 18 of the patch layer 1. After the step (1), the irradiation port 22 is disposed in opposed relation to the skin of the patient 20 at spaced intervals thereto.

3-2. Management Method of Patch (Step (2))

In the step (2), the irradiation port 22 applies at least one of the infrared light and the visible light in this manner, the radiation thermometer 13 detects a temperature change in the neighborhood in an irradiation direction of the irradiation port 22. That is, the radiation thermometer 13 detects a temperature change caused by sticking the patch layer 1 to the patient 20, that is, the temperature of the skin of the patient 20.

In the third embodiment, the same function and effect as that of the first embodiment can be achieved.

4. Fourth Embodiment

In the fourth embodiment, the same reference numerals are provided for members and steps corresponding to each of those in the first to third embodiments, and their detailed description is omitted.

In the first embodiment, as shown in FIG. 1, the sensor 7 is laminated in the patch layer 1 in the thickness direction.

Alternatively, in the fourth embodiment, as shown in FIG. 5, the sensor 7 is disposed next to the patch layer 1 in the first direction of the plane direction.

In the sensor 7, the solar cell layer 2 pressure-sensitively adheres to the skin of the patient 20 via a pressure-sensitive adhesive layer or the like that is not shown. The thermochromic resin layer 3 is laminated in the skin of the patient 20 in the thickness direction via the solar cell layer 2.

In the fourth embodiment, the same function and effect as that of the first embodiment can be achieved.

However, the first embodiment is preferable compared to the fourth embodiment.

In the first embodiment, as shown in FIG. 1, each of the: solar cell layer 2 and the thermochromic rosin layer 3 is laminated in the patch layer 1 in the thickness direction, so that the patch device 11 can be simply constituted from the patch layer 1, the solar cell layer 2, and the thermochromic resin layer 3. Also, the miniaturization of the patch device 11 can be achieved.

In the patch device 11, the heat from the patient 20 is conducted to the thermochromic resin layer 3 via the patch layer 1, so that a compact structure of the thermochromic resin layer 3 and the patch layer 1 can be achieved.

EXAMPLES

The specific numerical values in mixing ratio (content ratio), property value, and parameter used in the following description can be replaced with upper limit values (numerical values defined as "or less" or "below") or lower limit values (numerical values defined as "or more" or "above") of corresponding numerical values in mixing ratio (content ratio), property value, and parameter described in the above-described "DESCRIPTION OF EMBODIMENTS".

Example 1

1. Preparation of Management Module of Patch

As shown in FIG. 1, the management module 10 of a patch including the sensor-including patch laminate 17, the transmitter 4, the receiver 5, and the judgement device 8 was prepared. The sensor-including patch laminate 17 sequentially included the peeling sheet 25, the patch layer 1, the solar cell layer 2, and the thermochromic resin layer 3.

The patch layer 1 was made of 5.82 parts by mass of lidocaine (anesthetic) and 58.01 parts by mass of acrylic pressure-sensitive adhesive (acrylic polymer A of Japanese Unexamined Patent Application No. 2012-176942). The thickness of the patch layer 1 was 90 μm. The heat conductivity of the patch layer 1 was 0.3 W/m·K.

The solar cell layer 2 was a solar cell of an Amorton film (manufactured by Panasonic Eco Solutions Amorton Co., Ltd.). The thickness of the solar cell layer 2 was 300 μm.

The thermochromic resin layer 3 was prepared from 100 parts by mass of silicone resin (50 parts by mass of KE-109E-A and 50 parts by mass of KE-109E-B, manufactured by Shin-Etsu Chemical Co., Ltd.), and 7.5 parts by mass of thermochromic pigment (ETSD Powder, product number: ETSD 30, color changing point: 30° C., manufactured by JAPAN CAPSULAR PRODUCTS INC.). The thickness of the thermochromic resin layer 3 was 30 μm.

The receiver 5 was incorporated into the judgement device 8. The judgement device 8 included a speaker.

2. Step (1)

First, the peeling sheet 25 was peeled from the first main surface 19 of the patch layer 1, and exposed the first main surface 19 of the patch layer 1.

At this point, the judgement device 8 did not inform that the patch layer 1 was stuck to the patient 20.

Next, the first main surface 19 of the patch layer 1 was stuck to the skin of the patient 20, 3. Step (2) and Step (3)

Then, the heat from the patient 20 was conducted to the thermochromic resin layer 3 via the patch layer 1 and the solar cell layer 2, and the temperature of the thermochromic resin layer 3 was increased, so that the light transmittance of the thermochromic resin layer 3 was increased.

At this time, the solar cell layer 2 received the light, and generated an electromotive three. The solar cell layer 2 output the electromotive force as a detected signal. The transmitter 4 generated a patch signal based on the detected signal output from the solar cell layer 2, and wirelessly transmitted the patch signal. The receiver 5 received the patch signal wirelessly transmitted from the transmitter 4. Thereafter, the judgement device 8 informed that the patch layer 1 was stuck to the patient 20.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

The management method of a patch checks whether or not the patch is stuck to the skin of the patient.

DESCRIPTION OF REFERENCE NUMERALS

1 Patch layer
2 Solar cell layer
3 Thermochromic resin layer
4 Transmitter
5 Receiver
7 Sensor
8 Judgement device
10 Management module of patch
11 Patch device
12 Thermocouple thermometer
13 Radiation thermometer
20 Patient

The invention claimed is:
1. A patch device comprising:
a patch for being stuck to an individual having a body temperature, and
a sensor detecting a temperature change caused by sticking the patch to the individual,
wherein the sensor includes:
a temperature changing member generating a temperature change caused by sticking the patch to the individual, and
an output device outputting a detected signal based on the temperature change of the temperature changing member,
wherein
the temperature changing member is laminated in the patch,
heat from the individual is conducted to the temperature changing member via the patch,
the temperature changing member is a thermochromic resin layer made of a thermochromic resin having a light transmittance changeable according to a temperature change,
the output device is an electromotive force generating device that generates an electromotive force based on the temperature change of the temperature changing member,
the electromotive force generating device is a solar cell,
the solar cell is laminated in the patch,
the patch, the solar cell, and the thermochromic resin layer are disposed in order in a thickness direction,
a material of the thermochromic resin layer is a reversible thermochromic composition that becomes colorless in a temperature region of a color changing point or more, and colored in the temperature region of below a color changing point, and
the patch device is configured that:
before sticking the patch to the individual, the temperature of the thermochromic resin layer becomes below the color changing point, the thermochromic resin layer shields light to the solar cell layer, and the solar cell does not generate an electromotive force, and when the patch is stuck to the individual, heat from the individual is conducted to the thermochromic resin layer via the patch and the solar cell, the temperature of the thermochromic resin layer becomes the color changing point or more, the light transmits the thermochromic resin layer, the solar cell receives the light, and generates the electromotive force.

2. The patch device according to claim 1 further comprising:
a transmitting device connected to the solar cell.

3. A management module of a patch comprising:
a patch for being stuck to an individual having a body temperature,
a sensor detecting a temperature change caused by sticking the patch to the individual, and
a judgement unit judging whether or not the patch is stuck to the individual based on the detection of the sensor,
wherein the sensor includes:
    a temperature changing member generating a temperature change caused by sticking the patch to the individual, and
    an output device outputting a detected signal based on the temperature change of the temperature changing member,
    wherein
    the temperature changing member is laminated in the patch,
    heat from the individual is conducted to the temperature changing member via the patch,
    the temperature changing member is a thermochromic resin layer made of a thermochromic resin having a light transmittance changeable according to a temperature change,
    the output device is an electromotive force generating device that generates an electromotive force based on the temperature change of the temperature changing member,
    the electromotive force generating device is a solar cell,
    the patch, the solar cell, and the thermochromic resin layer are disposed in order in a thickness direction,
a material of the thermochromic resin layer is a reversible thermochromic composition that becomes colorless in a temperature region of a color changing point or more, and colored in the temperature region of below a color changing point, and
the patch device is configured that:
before sticking the patch to the individual, the temperature of the thermochromic resin layer becomes below the color changing point, the thermochromic resin layer shields light to the solar cell layer, and the solar cell does not generate an electromotive force, and
when the patch is stuck to the individual, heat from the individual is conducted to the thermochromic resin layer via the patch and the solar cell, the temperature of the thermochromic resin layer becomes the color changing point or more, the light transmits the thermochromic resin layer, the solar cell receives the light, and generates the electromotive force.

4. The management module of a patch according to claim 3, further comprising:
a transmitting device connected to the sensor, and
a receiving device connected to the judgement unit.

5. A management method of a patch for managing a sticking state of a patch with respect to an individual having a body temperature, the method comprising:
a step (1) of sticking the patch to the individual,
a step (2) of detecting a temperature change caused by sticking the patch to the individual, and
a step (3) of judging whether or not the patch is stuck to the individual based on a presence or absence of the temperature change,
wherein
the sensor includes:
    a temperature changing member generating a temperature change caused by sticking the patch to the individual, and
    an output device outputting a detected signal based on the temperature change of the temperature changing member,
    wherein
    the temperature changing member is laminated in the patch,
    heat from the individual is conducted to the temperature changing member via the patch,
    the temperature changing member is a thermochromic resin layer made of a thermochromic resin having a light transmittance changeable according to a temperature change,
    the output device is an electromotive force generating device that generates an electromotive force based on the temperature change of the temperature changing member,
    the electromotive force generating device is a solar cell,
    the patch, the solar cell, and the thermochromic resin layer are disposed in order in a thickness direction,
a material of the thermochromic resin layer is a reversible thermochromic composition that becomes colorless in a temperature region of a color changing point or more, and colored in the temperature region of below a color changing point, and
the patch device is configured that:
before sticking the patch to the individual, the temperature of the thermochromic resin layer becomes below the color changing point, the thermochromic resin layer shields light to the solar cell layer, and the solar cell does not generate an electromotive force, and
when the patch is stuck to the individual, heat from the individual is conducted to the thermochromic resin layer via the patch and the solar cell, the temperature of the thermochromic resin layer becomes the color changing point or more, the light transmits the thermochromic resin layer, the solar cell receives the light, and generates the electromotive force.

* * * * *